United States Patent [19]

Wurtman

[11] Patent Number: 4,624,852
[45] Date of Patent: Nov. 25, 1986

[54] PROCESS AND COMPOSITION FOR TREATING NEUROLOGICAL DISORDERS AND AGING

[75] Inventor: Richard J. Wurtman, Boston, Mass.

[73] Assignee: Massachusetts Institute of Technology, Cambridge, Mass.

[21] Appl. No.: 613,000

[22] Filed: May 21, 1984

Related U.S. Application Data

[62] Division of Ser. No. 495,202, May 15, 1983, abandoned.

[51] Int. Cl.$^4$ .................. A61K 31/40; A61K 31/195; A61K 31/685
[52] U.S. Cl. ...................................... 514/77; 514/76; 514/419; 514/567
[58] Field of Search .................. 424/199, 274, 319

[56] References Cited

U.S. PATENT DOCUMENTS

| 4,351,831 | 9/1982 | Growdon et al. | 424/199 |
| 4,355,027 | 10/1982 | Growdon et al. | 424/199 |
| 4,385,053 | 5/1983 | Reisberg et al. | 424/199 |
| 4,430,330 | 2/1984 | Growdon et al. | 424/199 |

*Primary Examiner*—Stanley J. Friedman
*Attorney, Agent, or Firm*—Paul J. Cook

[57] ABSTRACT

Choline or a choline precursor is administered to a patient together with an amino acid which is a precursor to a neurotransmitter in order to give a synergistic result for the two components.

10 Claims, No Drawings

PROCESS AND COMPOSITION FOR TREATING NEUROLOGICAL DISORDERS AND AGING

The Government has rights in this invention pursuant to a grant awarded by the National Institutes of Health.

This application is a division, of application Ser. No. 495,202, filed May 15, 1983, now abandoned.

This invention relates to a process for potentiating the effect of neurotransmitters in the brain.

In normal aging, the brain loses neurons, including those that are dependent on the diet and blood stream for the precursors of their neurotransmitters, for example, acetylcholine-releasing or "cholinergic" neurons, which make acetylcholine from dietary lecithin or circulating choline; "catecholaminergic" neurons, that make dopamine, norepinephrine, or epinephrine from tyrosine; "serotoninergic" neurons, that synthesize serotonin from tryptophan; or "glycinergic" neurons, that can produce glycine from the amino acid threonine. Neuronal cell loss is specifically exacerbated in particular neurological diseases, such as senility or Alzheimer's Disease in which cholinergic neurons are especially deficient, but catecholaminically affects dopaminergic neurons. Unfortunately, there is no presently available means to determine in a particular normal old person, or a person with a neurological disease, how many of which neuronal types have been lost. Moreover, a treatment that replaces one of the deficient neurotransmitters might be of limited utility if another transmitter were also deficient. Ideally, a treatment for this neuronal loss would provide the brain with agents that could increasae the synthesis and release any of several transmitters, but which would have an effect only if each transmitter's release were deficient.

It is known that giving experimental animals choline enhances acetylcholine synthesis in rapidly-firing cholinergic neurons, and therefore is useful in treating disease states characterized by inadequate acetylcholine release, for example, Alzheimer's Disease, in which the surviving neurons presumably fire frequently, to make up for the missing ones, and also as a supplement to drugs which either act by releasing acetylcholine or which, as a side-effect, deplete neurons of acetylcholine. It is also known that giving tyrosine similarly enhances catecholamine release from rapidly-firing neurons, and that giving tryptophan or threonine enhances serotonin or glycine production in serotoninergic or glycinergic neurons, respectively. It is also known that the effectiveness of giving any of these amino acids can be potentiated by providing the amino acid in the proper ratio to carbohydrates which elicit insulin secretion, and which thereby lower plasma levels of other amino acids that compete with the desired one for uptake into the brain.

It would be desirable to provide a means of potentiating the effect of neurotransmitter precursors when administered to a patient. In order to obtain a synergistic effect (greater than an additive effect) when a combination of neurotransmitter precursors are administered to a patient, four conditions must exist, as exemplified by the interactions of tyrosine and choline. First, it is known that within a brain region such as corpus striatum, direct reciprocal synapses must exist between dopaminergic cells and e.g., cholinergic cells (in the case of tyrosine and choline). Second, it is known that cholinergic cells and dopaminergic cells both have the property of making and releasing more of their neurotransmitters when exposed to greater amounts of the precursor if the cells are firing frequently. Prior to this invention, it was not known that the necessary third and fourth conditions existed. The third condition is that acetylcholine release by the cholinergic cells must increase the firing of the dopaminergic cells, thereby making them tyrosine dependent. The fourth condition is that the loss of some dopaminergic neurons such as by aging or disease also causes the surviving dopaminergic neurons to fire frequently and thus become tyrosine-dependent.

SUMMARY OF THE INVENTION

This invention is based upon the discovery that the concomitant administration of (a) choline or a choline precursor and (b) an amino acid which is a precursor to a neurotransmitter, i.e., tyrosine, tryptophan or threonine results in increased release of both their corresponding neurotransmitters, i.e., (a) acetylcholine and (b) dopamine, serotonin or glycine. The choline or choline precursor and amino acid are administered to a patient concomitantly. The coadministration of these compositions is particularly useful for patients affected by neurological disease including senility, Alzheimer's Disease or Parkinson's Disease, but also in normal older people, or people with obscure deficits in neurons releasing particular neurotransmitters.

DETAILED DESCRIPTION OF SPECIFIC EMBODIMENTS

In accordance with this invention, choline or a compound that dissociates to form choline is orally administered to a patient prior to or together with an amino acid which is a precursor to a neurotransmitter, in order to increase blood levels of choline and the amino acid, and thereby to increase the levels of acetylcholine and the other neurotransmitter in the brain. The acetylcholine is synthesized from choline and acetyl CoA in a reaction catalyzed by choline acetyltransferase (CAT); the amino acid is converted to the other neurotransmitter by another enzyme. It has been found that the coadministration of choline or a compound that dissociates to form choline, and the amino acid, potentiates the neurological effects of both the amino acid and the choline or choline precursor.

The choline can be administered as choline salts or esters, such as the chloride bitartrate or stearate or the like, or as a compound that dissociates to choline, such as sphingomyelin, cytidine-diphospho-choline, an acyl-glycerophosphocholine, e.g., lecithin, lysolecithin, glycerophosphatidyl choline, mixtures thereof or the like. By the term acylglycerophosphocholine as used herein is meant a compound of the formula:

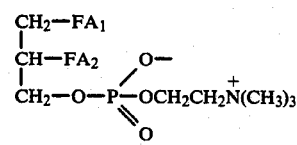

wherein $FA_1$ and $FA_2$ can be the same or different and are fatty acid residues having from 6–26 carbon atoms, usually 16–24 carbon atoms and can be saturated or unsaturated such as palmitic acid, palmitoleic acid, stearic acid, oleic acid, linoleic acid, eicosenoic acid, arachidonic acid, docosahexaenoic acid, eicosapentaenoic acid, linolenic acid, mixtures thereof or the like. The fatty acid residues of the acylglycerophosphocholine can be varied easily by reacting the acylglycerophosphocholine, e.g., a lecithin with phospholipase A1 or A2 (to cleave one fatty acid residue) or then phospholipase B (when desired to cleave both fatty acid residues) and then reacting the cleaved compound with the fatty acid of choice. These choline producing compounds also can be administered to patients having lower than normal plasma choline levels, such as patients experiencing renal dialysis. It is preferred to employ an acylglycerophosphocholine, e.g., lecithin as the choline source since it is not degraded in the gut in contrast to choline. The choline or compound that dissociates to choline is administered so that a choline level of at least about 20–30 nanomoles/ml and usually between about 10 and 50 n moles/ml is attained in the patient's bloodstream. For example, when administering choline chloride in the form of capsules or tablets, suitable dosages are from about 1 to 30 g/day, preferably 3–20 g/day taken in divided doses 500 to 1000 mg/cap or tab. When choline chloride is administered in liquid form admixed with a conventional liquid carrier such as a sweetened elixir or the like, from about 1 to 10 grams/15 ml, preferably from about 2 to 5 grams/15 ml can be utilized. When utilizing lecithin in a liquid carrier, it is administered in amounts of between about 0.1 and 50 grams/day. When lecithin is administered in granular form, as a tablet or in a capsule, it is employed in amounts of between about 0.1 and 100 g/day, usually between about 30 and 50 g/day. Normally, lecithin is not available as a pure compound and is available in admixture with other phospholipids wherein the lecithin comprises about 20–30 weight percent of the mixture.

In the process of this invention, the choline or compound that dissociates to choline is administered concomitantly with the amino acid. The administration of the compositions employed in the present invention can be effected orally, interperitoneally, subcutaneously, intravenously or intramuscularly; the amino acids, tyrosine or tyrosine precursor (phenylalanine), threonine or tryptophan, can be used as such, as salts or esters, as peptides or as compounds which are metabolized to give the amino acids in vivo (e.g., alpha-keto amino acids). Conveniently, the compositions employed in this invention are admixed or dissolved in any innocuous vehicle such as water or sterile saline solution or in tablet or powder form containing the usual solid diluents or carriers, or as foods or enteral nutrition mixtures. The compositions employed in the present invention are administered in concentrations to avoid undesirable side effects. In humans, useful dosages of tyrosine are between about 0.5 mg/kg and 250 mg/kg (depending on route of administration), preferably between about 0.5 mg/kg and 50 mg/kg when given intravenously and 10 mg/kg and 200 mg/kg when given orally. (Threonine and tryptophan doses are similar). The administration of tyrosine or phenylalanine should, if possible, be made in the absence of other amino acids that might compete for uptake in the brain and which themselves do not produce dopamine. When tryptophan is administered, it can be administered with caffeine or another mild stimulant to suppress its effect on sleepiness. Also, the amino acid can be administered with an insulin-releasing carbohydrate such as sucrose, glucose or the like in order to lower plasma levels of leucine, isoleucine and valine which would otherwise compete for brain uptake.

The following example illustrates the present invention and is not intended to limit the same.

EXAMPLE I

A study was done on rats to show that the concurrent administration of choline with tyrosine produced effects that were much greater than the sum of their individual effects, i.e., that they potentiated each other. Adult male Sprague-Dawley rats were given lesions on one side of the brain; the other side served as a normal control (and had been shown previously to be unaffected by the unilateral lesion). The lesion partially destroyed the dopaminergic neurons running from the substantia nigra to the corpus striatum (i.e., the neurons whose loss is most responsible for Parkinson's Disease in humans, but which also are deficient in "normal" old people). It has previously been shown that when 75% of the neurons are destroyed, the surviving nigrostriata neurons respond by increasing the frequency with which they fire. Up to a point this suffices, and the animal, or a human with a corresponding loss, does not show symptoms except when stressed; however, beyond a 50–60% lesion, symptoms appear generally. It also has been previously shown that, in such animals, giving supplemental tyrosine had no effect on dopamine synthesis or release (as estimated by measuring the levels of the dopamine metabolites HVA, homovanillic acid, and DOPAC, dihydroxyphenylacetic acid, in the striatum), but did enhance its synthesis and release in the lesioned side.

About a week after placement of the unilateral lesions, animals received either choline chloride (10 nmoles/kg) alone, or tyrosine alone (250 mg/kg), or both, and were killed an hour later; HVA and DOPAC were measured in striata from the unlesioned and lesioned sides (Table I). In the unlesioned side, neither tyrosine alone nor choline alone enhanced dopamine release (i.e., as reflected in striatal level of its metabolites HVA and DOPAC). However, giving both compounds did cause significant increases in the metabolites. On the lesioned side, tyrosine alone did, as shown previously, enhance dopamine release (increasing DOPAC from 0.11 to 0.19, and HVA from 0.08 to 0.14); choline alone was without effect. Giving the two precursors caused a vastly greater increase in dopamine release (elevating DOPAC to 0.28 and HVA to 0.24). The potentiation of tyrosine's effect by choline most likely reflects increased acetylcholine release within the striatum itself; the acetylcholine then acts, trans-synaptically or via presynaptic receptors. Since serotoninergic, noradrenergic, and glycinergic neurons appear also to make synaptic contacts with cholinergic neurons, it is apparent that raising blood choline levels will also potentiate the effects of giving their precursors (tryptophan, tyrosine, threonine). Again, the brain will "decide" whether any neurons respond by modulating their firing frequencies.

The ability of tyrosine-plus-choline to enhance dopamine release in the "normal", unlesioned side, provides evidence that mixtures of the precursors will have useful effects in people without overt neurological diseases (e.g., old people who have lost some neurons, but too few to cause overt symptoms; children and young adults with "minimal brain dysfunction").

TABLE I

EFFECT OF CHOLINE PLUS TYROSINE ON DOPAMINE METABOLITES IN RAT CORPUS STRIATUM

| Treatment | Unlesioned Side | | Lesioned Side | |
| --- | --- | --- | --- | --- |
| | DOPAC | HVA | DOPAC | HVA |
| control | 0.52 | 0.48 | 0.11 | 0.08 |
| tyrosine | 0.51 | 0.50 | 0.19* | 0.14* |
| choline | 0.56 | 0.53 | 0.12 | 0.08 |
| tyrosine & choline | 0.66* | 0.58* | 0.28** | 0.24** |

Animals received choline chloride (10 nmoles/kg p.o.), tyrosine (250 mg/kg, i.p.) or both 5-8 days after placement of a partial unilateral nigrostriatal lesion (with 6-hydroxydopamine); they were killed one hour later. Data are given as nanograms/mg tissue.

*$P < 0.05$ differs from corresponding control tissue
**$P < 0.01$ differs from corresponding control tissue

I claim:

1. The process for relieving the adverse effects of neurological disease or aging in a patient, which comprises administering a composition comprising (a) tryptophans and (b) an amount of a compound effective to raise the blood stream choline level of a patient to between about 10 and 50 nanomoles/ml and to release adequate amount of brain acetylcholine selected from the group consisting of choline, a choline salt, a choline ester, sphingomyelin, cytidine-diphospho-choline and an acylglycerocholine of the formula:

$$\begin{array}{l} CH_2-FA_1 \\ | \\ CH-FA_2 \quad O- \\ | \quad\quad\quad / \\ CH_2-O-P-OCH_2CH_2\overset{+}{N}(CH_3)_3 \\ \quad\quad\quad \backslash\!\!\backslash \\ \quad\quad\quad\quad O \end{array}$$

wherein $FA_1$ and $FA_2$ can be the same or different and are fatty acid residues having from 6–26 carbon atoms, and mixtures thereof.

2. The process of claim 1 wherein the choline precursor is an acylglycerophosphocholine.

3. The process of claim 1 wherein the choline precursor is lecithin.

4. The process of claim 1 wherein the choline precursor is choline chloride.

5. The process of claim 1 wherein the choline precursor is cytidine-diphosphocholine.

6. A composition of matter comprising (a) tryptophan and (b) an amount of a compound effective to raise the bloodstream choline level of a patient to between about 10 and 50 nanomoles/ml and to release adequate amounts of brain acetylcholine selected from the group consisting of choline, a choline salt, a choline ester, sphingomyelin, cytidine-diphospho-choline and an acylglycerophosphocholine of the formula:

$$\begin{array}{l} CH_2-FA_1 \\ | \\ CH-FA_2 \quad O- \\ | \quad\quad\quad / \\ CH_2-O-P-OCH_2CH_2\overset{+}{N}(CH_3)_3 \\ \quad\quad\quad \backslash\!\!\backslash \\ \quad\quad\quad\quad O \end{array}$$

wherein $FA_1$ and $FA_2$ can be the same or different and are fatty acid residues having from 6–26 carbon atoms, and mixtures thereof.

7. The composition of claim 6 wherein the choline precursor is an acylglycerophospho-choline.

8. The composition of claim 6 wherein the choline precursor is lecithin.

9. The composition of claim 6 wherein the choline precursor is choline chloride.

10. The composition of claim 6 wherein the choline precursor is cytidine-diphosphocholine.

* * * * *